United States Patent
Doran et al.

(10) Patent No.: US 6,608,202 B1
(45) Date of Patent: Aug. 19, 2003

(54) PROCESS OF SYNTHESIS OF A TRICYCLIC KETONE INTERMEDIATE

(75) Inventors: Henry J. Doran, Bray (IE); Pat M. O'Neill, Arklow (IE); Robert P. Williams, Enniskerry (IE)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/223,799

(22) Filed: Aug. 20, 2002

(65) Prior Publication Data

US 2003/0144314 A1 Jul. 31, 2003

Related U.S. Application Data

(60) Provisional application No. 60/313,758, filed on Aug. 21, 2001.

(51) Int. Cl.[7] ............... C07D 221/06; C07D 213/24
(52) U.S. Cl. .................................. 546/93; 546/326
(58) Field of Search .................... 546/93, 326

(56) References Cited

U.S. PATENT DOCUMENTS

| | | |
|---|---|---|
| 4,659,716 A | 4/1987 | Villani et al. |
| 4,731,447 A | 3/1988 | Schumacher et al. |
| 6,271,378 B1 | 8/2001 | Doran et al. |
| 6,372,909 B1 | 4/2002 | Bernard et al. |
| 6,492,519 B2 | 12/2002 | Poirier et al. |

FOREIGN PATENT DOCUMENTS

| | | |
|---|---|---|
| WO | WO 96/31478 | 10/1996 |
| WO | WO 00/05215 | 2/2000 |
| WO | 00/05215 | * 2/2000 ............... 546/93 |

OTHER PUBLICATIONS

J. Epsztajn et al., "Application of Organolithium and Related Reagents in Synthesis. Part 11[1] Metallation of 2–Methyl– and 4–Methylnicotinic Acids A Useful Method for Preparation of AZA–Isocoumarins" *Synthetic Communications* 22(9) 1239–1247 (1992).

Creger P.L., et al. "Metalated Carboxylic Acids II. Monoalkylation of Metalated Toluic Acids and Dimethylbenzoic Acids" *Journal of the American Chemical Society*, 92(5) 1396–1397 (1970).

* cited by examiner

*Primary Examiner*—Charanjit S. Aulakh
(74) *Attorney, Agent, or Firm*—William Y. Lee

(57) ABSTRACT

In one embodiment, the present invention describes the synthesis of a compound of Formula III, wherein X is halogen,

III

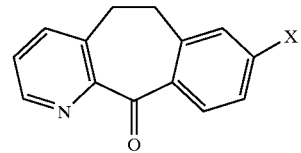

and intermediates therefor from easily available starting materials by a simple route.

20 Claims, No Drawings

PROCESS OF SYNTHESIS OF A TRICYCLIC KETONE INTERMEDIATE

CROSS REFERENCE TO RELATED APPLICATIONS

This application claims the benefit of priority of U.S. Ser. No. 60/313,758 filed Aug. 21, 2001.

FIELD OF THE INVENTION

The present invention relates to a process for the synthesis of a tricyclic ketone of Formula III, wherein X is halogen:

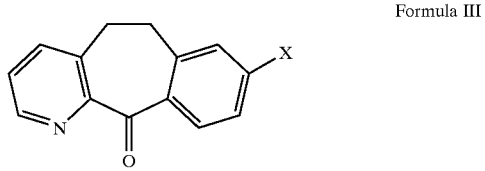

Formula III

The compound of formula III is an intermediate useful in the production of antihistamines and other compounds.

BACKGROUND OF THE INVENTION

Several methods are known in the art for synthesizing tricyclic ketones. For example, a compound of Formula VI,

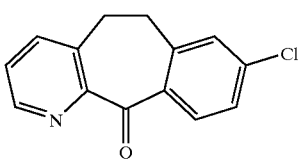

Formula VI (8-Chloro-5,6-dihydro-11H-benzo[5,6]cyclohepta[1,2-b]pyrid-11-one) is described in U.S. Pat. No. 6,271,378 as an intermediate used in the synthesis of the antihistamines loratadine and desloratadine.

U.S. Pat. No. 4,731,447 describes the synthesis of the compound of Formula VI in three steps from N-tert-butyl-3-methyl-picolinamide. The first step involves the alkylation of the amide with 3-chlorobenzyl chloride to form a tert-butyl amide, which on hydrolysis, using, e.g., sulfuric acid, forms 3-[2-(3-chlorophenethyl)] picolinic acid. Cyclization to the ketone is effected under Friedel-Crafts conditions using, e.g., anhydrous HCl with oxalyl chloride and aluminum chloride (AlCl₃) in tetrachloroethane as the solvent.

An alternative process to synthesize a compound of Formula VI is disclosed in PCT Publication WO96/31478. This involves the conversion of the tert-butyl amide to a nitrile using POCl₃ in toluene. The nitrile can be cyclized to an imine, which on hydrolysis gives the desired compound.

U.S. Ser. No. 09/442,512 discloses a three-step process for the synthesis of a compound of Formula VI in which 3-methylpicolinic acid or 2-bromo-3-methylpyridine is converted to an anilide. The anilide is alkylated with 3-chlorobenzyl chloride to give an anilide, which can be converted to a tricyclic ketone using a dehydrating agent, e.g., PCl₅, and a Lewis acid, e.g., AlCl₃, via an intermediate imine. A tricyclic ketone of Formula VI is formed from the hydrolysis of this imine.

U.S. Ser. No. 09/836,605 discloses the following process to prepare a tricyclic ketone of Formula VI, wherein M is a metal, $R^1$ is, but not limited to a group such as alkyl, aryl or cycloalkyl, L is a leaving group and R is H or chloride:

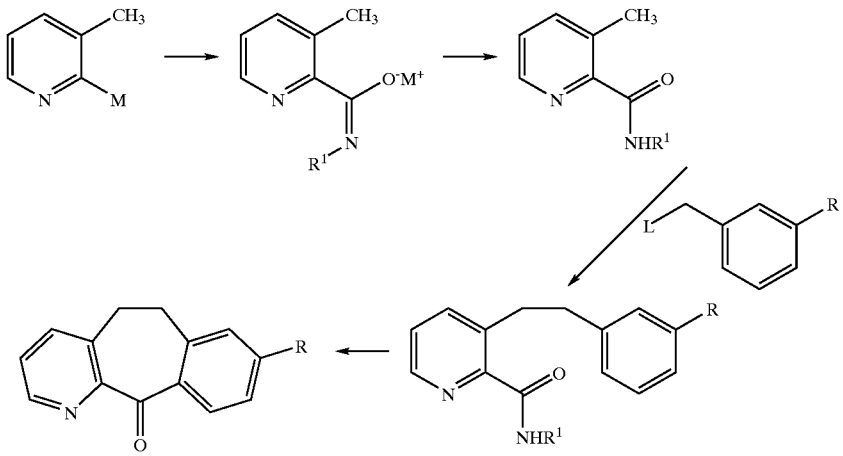

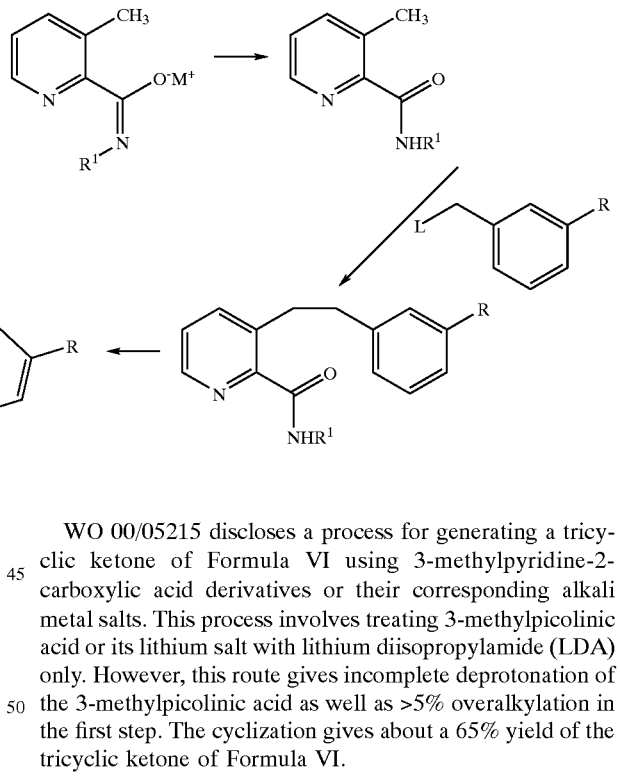

WO 00/05215 discloses a process for generating a tricyclic ketone of Formula VI using 3-methylpyridine-2-carboxylic acid derivatives or their corresponding alkali metal salts. This process involves treating 3-methylpicolinic acid or its lithium salt with lithium diisopropylamide (LDA) only. However, this route gives incomplete deprotonation of the 3-methylpicolinic acid as well as >5% overalkylation in the first step. The cyclization gives about a 65% yield of the tricyclic ketone of Formula VI.

J. Epsztajn et al., Synthetic Communications 22(9) 1239–1247 (1992) describe the preparations of dianions of 2-methyl and 4-methylnicotinic acids using LDA alone.

In view of the importance of antihistamines such as loratadine and desloratadine, new novel methods of making intermediates for the synthesis of said antihistamines are always of interest.

SUMMARY OF THE INVENTION

In an embodiment, the present application teaches a novel, simple process of making a compound of Formula III. The compound of Formula III is prepared from a compound of Formula I:

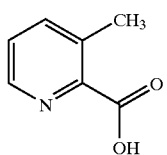

Formula I

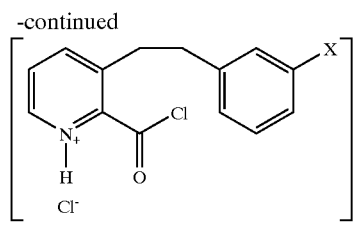

Formula IIb and c) cyclizing the compound of Formula IIb into the compound of Formula III:

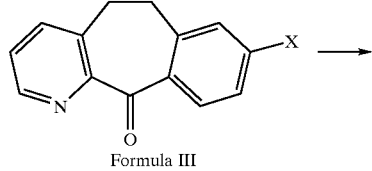

Formula IIb

The process of making a compound of Formula III wherein X is halogen,

Formula III

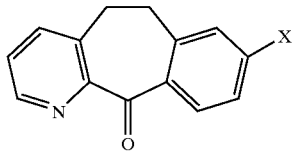

and pharmaceutically acceptable salts thereof, comprises:

a) alkylating a compound of Formula I:

Formula I

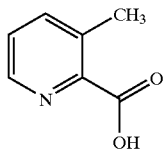

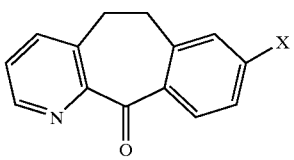

Formula III the steps b) and c) being done in one pot.

The tricyclic ketone of Formula III prepared by the present process is a useful intermediate, especially for the synthesis of antihistamines. For example, U.S. Pat. No. 6,271,378 describes the synthesis of the antihistamine of Formula VII:

with a compound of formula Y-X, where Y is an arylalkyl group, and X is a halogen, in the presence of a lithium amide and an additional base, to form an acid hydrochloride compound of Formula IIa:

Formula IIa

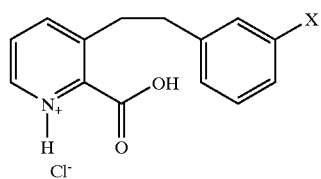

b) converting the acid hydrochloride of Formula IIa into the intermediate (an acyl chloride hydrochloride) of Formula IIb:

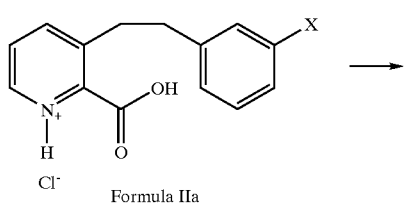

Formula IIa

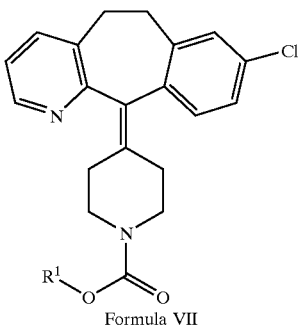

Formula VII wherein $R^1$ is substituted or unsubstituted alkyl, alkenyl, aryl, aralkyl, cycloalkyl or cycloalkylalkyl.

The inventive process to make the compound of Formula III has several advantages. The claimed invention dispenses with the N-tert-butyl amide or anilide groups that act essentially as protecting/activating groups in the alkylation of the compound of Formula I, thus leading to a direct alkylation of the compound of Formula I. Further, Formula IIa is isolated as the hydrochloride directly by addition of an excess of hydrochloric acid during the workup of the alkylation reaction. The use of pre-formed hydrochloride, as well as the employment of a catalytic quantity of Vilsmeier's reagent, significantly improves the conversion of IIa to IIb. Also the use of high purity acid hydrochloride of Formula IIa, permits the isolation of the ketone of Formula III through a simple pH adjustment, thus eliminating the need for a less efficient and environmentally less favorable crystallization from an organic solvent or mixture of solvents. The more concentrated volumes of solvents used increases the efficiency of the present process while at the same time reducing the volumes of the waste streams in comparison to previously used methods.

DESCRIPTION OF THE INVENTION

In one embodiment, the present invention discloses a novel, easy-to-use process for preparing the compound of Formula IIII. The inventive process is schematically described in Scheme I:

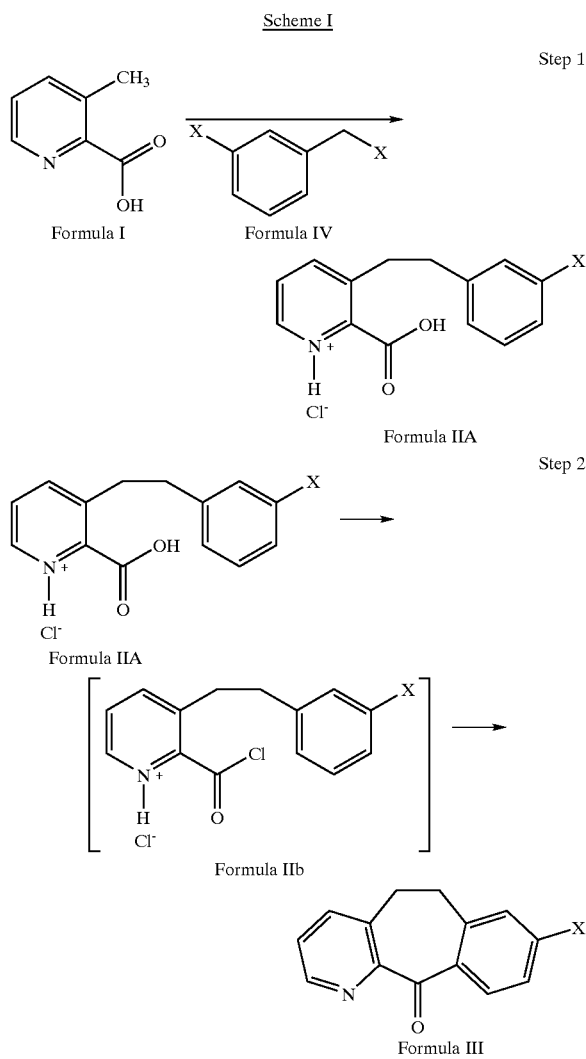

The moiety X is a halogen, preferably chlorine.

In Step 1 of the claimed process, the compound of formula I is alkylated with an arylalkyl halide to form the compound of Formula IIa. Preferred arylalkyl halide is a compound of X-Y where X is a halogen and Y is arylalkyl. Preferred arylalkyl halide is a compound of Formula IV

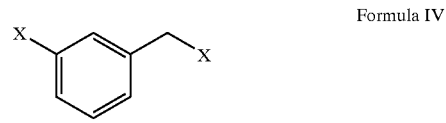

The compound of Formula I is preferably alkylated in the presence of a lithium amide, preferably lithium diisopropylamide (LDA) or lithium dialkylated amide and an additional base of formula M—Ot—Bu, where M is sodium or potassium. A preferred mole ratio of the compound of Formula I to LDA to M—Ot—Bu is 1:2:1. The compound of formula I can also be mixed with a solvent, lithium amide base and the base of formula M—Ot—Bu. Preferred solvents are THF or triethylamine. The mixture of Step 1 is acidified with, preferably, HCl. The end product of Step 1 is either isolated as the free acid (Formula II)

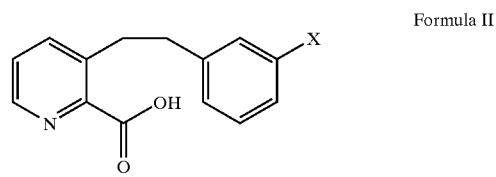

or as the hydrochloride salt (Formula IIa), depending on the quantity of hydrochloric acid used in the acidification. Additionally, during Step 1, the reaction mixture can be quenched with water or, preferably, an aqueous sodium or potassium carbonate solution., Typically, Step 1 of the claimed process occurs at a temperature range of from about to −40° C. about 30° C. The compound of Formula IIa can be isolated by suspending said compound of Formula II in water to form a mixture, acidifying said suspended compound with 37% HCl, heating said mixture to about 70° C., cooling said mixture to between about 0° C. and about 5° C., filtering said mixture and drying said mixture at about 60° C. to about 70° C. to yield said compound of Formula IIa. Using the method outlined in Step 1, a yield of 80–90% for the intermediate, 3-(3-chlorophenethyl) picolinic acid hydrochloride (Formula IIa) is obtained, while contaminates such as the dialkylated acid product (Formula IIc)

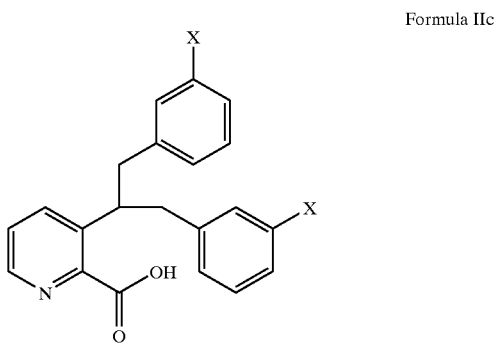

are minimized to levels <0.5%.

In Step 2 of the claimed process, the compound of Formula IIa is converted into the compound of Formula IIb, preferably in the presence of Vilsmeier's reagent (chloromethylenedimethylammonium chloride). The compound of Formula IIb is then cyclized into the compound of Formula III. The conversion of the compound of Formula IIa to the compound of Formula IIb and subsequently to the compound of Formula III takes place in the same pot. The process of Step 2 preferably takes place in the presence of a solvent, preferably dichloromethane. The solvent, oxalyl chloride, dimethylformamide, preferably 2 mole % with respect to the amount of the compound of Formula IIa and aluminum chloride form a reaction mixture. Upon formation of the compound of Formula III, it can be isolated from said reaction mixture by quenching with ice and sodium hydroxide followed by concentration of the organic layer. The compound of Formula III is extracted as a hydrochloride salt with hydrochloric acid to form an acid extract containing said compound of Formula III. The acid extract can then be filtered with charcoal and the compound of Formula III is separated from the acid extract by adjusting the pH of the acid extract to >7. The yield of Formula III in Step 2 is about 90% in the entire one-pot reaction, while levels of the contaminate, the 10-chloroisomer of Formula IIIa

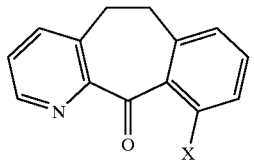

Formula IIIa are less than 0.5%.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl. "Aryl" means an aromatic monocyclic or multi-cyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfonyl, arylsulfonyl, heteroarylsulfinyl, alkylthio, arylthio, heteroarylthio, aralkylthio, heteroaralkylthio, cycloalkyl, cycloalkenyl, heterocyclyl, heterocyclenyl. Non-limiting examples of suitable aryl groups include phenyl and naphthyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Arylalkyl" means aryl and alkyl as defined above wherein one or more hydrogen atoms on the aryl is replaced by an alkyl group defined above. A non-limiting example of an arylalkyl is a compound of Formula IV, wherein X is a halogen.

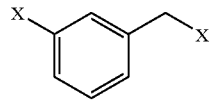

Formula IV

"Base" means compounds but are not limited to bases such as NH$_4$OH, KHCO$_3$, K$_2$CO$_3$, NaHCO$_3$, Na$_2$CO$_3$, NaOH, KOH or LiOH, or a base of formula M—Ot—Bu, where M is a metal, preferably sodium or potassium.

"Acid" means a protic acid, such as H$_2$SO$_4$ or CH$_3$SO$_3$H, or a Lewis acid such as AlCl$_3$.

"Deprotecting" means removal of a group from another group by a suitable reagent.

"Lithium amide" means those amides of lithium, including but not limited to LiNH$_2$, lithium dialkylated amides and lithium diisopropylamide.

"Vilsmeier's reagent" means a reagent of chemical formula of $(CH_3)_2N^+=CHCl(Cl)^-$ (chloromethylenedimethylammonium chloride).

While the preferred reagents and reaction conditions for the various steps are described in detail in the Examples section, the following summarizes the details.

The process starts with the compound of Formula I, 3-methylpicolinic acid, commercially available from Sigma Aldrich, St. Louis, Mo. In Step 1 of Scheme I, the direct alkylation of the compound of Formula I with a compound of Formula Y-X, where Y is an arylalkyl group and X is a halogen, in the presence of a lithium amide and an additional base to form the acid hydrochloride compound of Formula IIa. Examples of suitable lithium amides include those amides of lithium, including but not limited to LiNH$_2$, lithium dialkylated amides and lithium diisopropylamide (LDA). Examples of suitable additional bases include, but are not limited to bases such as NH$_4$OH, KHCO$_3$, K$_2$CO$_3$, NaHCO$_3$, Na$_2$CO$_3$, NaOH, KOH or LiOH, or a t-butoxide of formula M—Ot—Bu, where M is a metal, preferably sodium or potassium. Using LDA as a base, a direct alkylation of 3-methylpicolinic acid (Formula I) with 3-chlorobenzyl chloride (Formula IV) results in the formation of the key intermediate, 3-(3-chlorophenethyl)-picolinic acid. Additionally, an aqueous quench can take place during Step 1 to prevent the formation of the water-insoluble lithium salt of Formula II, which makes processing difficult. Examples of the aqueous quench solution can contain potassium carbonate or sodium carbonate. Use of the aqueous quench also results in an 80% recovery of lithium as lithium carbonate.

Previously described processes to form tricyclic ketones, such as those of Formula III, required the alkylation of N-t-butyl-3-methylpicolinamide, (see U.S. Pat. No. 4,731, 447) or anilide with 3-chlorobenzyl chloride to give N-t-butyl-3-(3-chlorophenethyl)-picolinamide or its anilide analogue (see U.S. Pat. No. 6,271,378). The tert-butyl amide is either hydrolyzed to the key intermediate using strongly acidic conditions or converted to the nitrile using a dehydrating agent. N-t-butyl-3-methylpicolinamide itself is prepared from 3-methylpicoline-N-oxide by a 2-step synthesis. In the case of the anilide, a separate synthetic step is required for its preparation from 3-methylpicolinic acid. The present invention dispenses with the N-tert-butyl amide or anilide groups that act essentially as protecting/activating groups in the lithiation/alkylation reaction. The present invention eliminates the need for the preparation of these derivatives of the 3-methylpicolinic acid. Also, 80% of the lithium is recovered as lithium carbonate.

Reaction Step 2 is a cyclization of the compound of Formula IIa into the compound of Formula III in one pot. Generally, the compound of Formula IIa is converted to the intermediate compound of Formula IIb, followed by ring closure of the intermediate compound of Formula IIb to form the compound of Formula III in one pot. In the present invention, considerable improvements have been made to the cyclization of the carboxylic acid hydrochloride of Formula IIa. Specifically, Formula IIa is converted into the acyl chloride hydrochloride of Formula IIb by treatment with 2 mole % of pre-formed Vilsmeier's reagent in a suitable solvent such as dichloromethane. This procedure decreases the time of formation of the intermediate acyl chloride of Formula IIb and improves the color of the resulting compound of Formula III. Analysis of a quenched sample of the acid chloride into a mixture of diethylamine in dichloromethane by thin-layer chromatography and HPLC indicates that the acyl chloride hydrochloride of Formula IIb is formed in greater than 99% yield assuming quantitative conversion to the diethylamide. The intermediate acyl chloride hydrochloride is then converted to the desired ketone (Formula III) by reaction with aluminum chloride. The reaction proceeds to completion by stirring overnight at room temperature. The ketone is isolated by quenching the reaction mixture onto ice/aqueous sodium hydroxide followed.by concentration of the organic layer. The ketone is extracted as the hydrochloride salt into dilute aqueous hydrochloric acid. The acidic extract is treated with decolorizing charcoal, filtered and the ketone is liberated in greater than 99% purity by a simple precipitation after adjustment of the pH to >7. The aqueous waste stream, containing sodium aluminate, can be treated efficiently by adjusting the pH to 7 by bubbling carbon dioxide through the solution resulting in the precipitation of aluminum hydroxide in a readily filterable form. The isolated yield of >99% pure ketone (Formula III) is about 90% from the hydrochloride of 3-(3-chlorophenethyl)-picolinic acid IIa.

The tricyclic ketone of Formula III may be isolated by procedures well known to those skilled in the art or preferably as described in the EXAMPLES section.

If desired, the compound of Formula III may be further converted to the desired antihistamines by suitable procedures known to those skilled in the art.

The products of the various steps in the reaction schemes described herein may be isolated and purified by conventional techniques such as, for example, filtration, recrystallization, solvent extraction, distillation, precipitation, sublimation and the like, well known to those skilled in the art. The products may be analyzed and/or checked for purity by conventional methods well known to those skilled in the art such as, for example, thin layer chromatography, NMR, HPLC, melting point, mass spectral analysis, elemental analysis and the like.

The following nonlimiting EXAMPLES are provided in order to further illustrate the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Certain substituents, solvents and reagents are referred to herein by the following abbreviations:

lithium diisopropylamide (LDA);

n-butyl lithium (n-BuLi);

dichloromethane (DCM);

dimethylformamide (DMF);

tetrahydrofuran (THF);

methyl (Me);

ethyl (Et);

butyl (Bu);

phenyl (Ph), metal atom (M);

t-butoxide (Ot-Bu);

aluminum chloride ($AlCl_3$);

and triethylamine ($NEt_3$).

An example of the claimed invention where X is Cl, is described below in Scheme 2, followed by the experimental details.

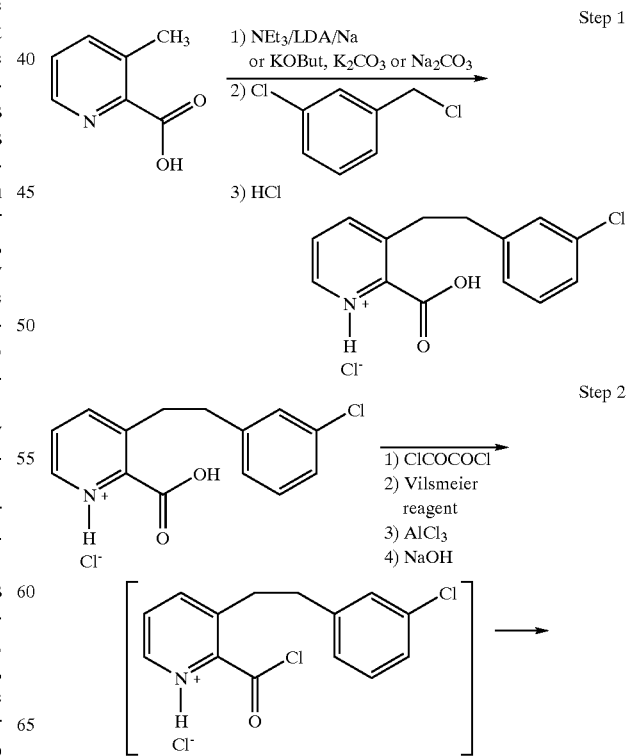

Scheme 2

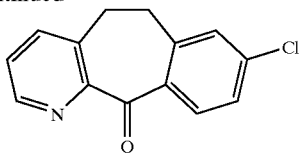

Example 1

Synthesis of 3-(3-Chlorophenethyl)-picolinic Acid Hydrochloride (3-CPPA.HCL) (Formula IIa)

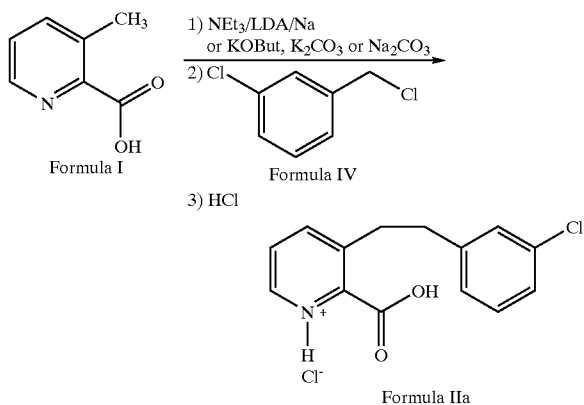

A mixture of THF (1050 mL) and diisopropylamine (320 mL, 2.29 mol) was cooled to 0° C., and potassium tert-butoxide (129 g, 1.095 mol; 95% pure) was added. The solution was cooled to −50° C. and n-butyllithium solution (2.5M in hexane, 925 mL, 2.312 mol) was added, keeping the temperature below −40° C. The solution was then stirred at −50° to −40° C. prior to the addition of a solution of 3-methylpicolinic acid of Formula I (150 g, 1.095 mol) in THF (300 mL) and triethylamine (55.3 g, 0.547 mol) at −45° to −35° C. Use of the triethylamine reduces the amount of THF needed to dissolve the compound of Formula I. The purple solution was stirred at −45° to −35° C., and 3-chlorobenzyl chloride of Formula IV (176.3 g, 1.095 mol) was added. The suspension was allowed to warm to ambient temperature overnight. The suspension was poured into a solution of potassium carbonate (150 g, 1.09 mol) in water (1150 mL), washed with an additional 200 mL of water and stirred. The suspension was filtered and the solid washed with 200 mL water. The bottom phase containing the product as the potassium salt was separated and the organic phase, washed with 100 mL water. The aqueous-solution was heated under vacuum to 60° C. to remove dissolved organic volatiles and cooled to 40° C. Concentrated hydrochloric acid (585 mL of 37%) was slowly added. The resulting suspension was cooled to 0° to 10° C., filtered and washed with 10% aqueous HCl (200 mL) to remove salts. The suspension was washed with acetone and dried to give 286.5 g (88%) of 3-(3-chlorophenethyl)-picolinic acid hydrochloride 3-CPPA.HCl (Formula IIa).

Example 2

Synthesis of 8-Chloro-5,6-dihydro-11H-Benzo[5,6]cyclohepta[1.2-b]pyridin-11-one. (8-Chloro-ESC-Ketone) (Formula III)

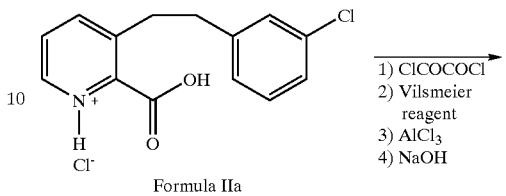

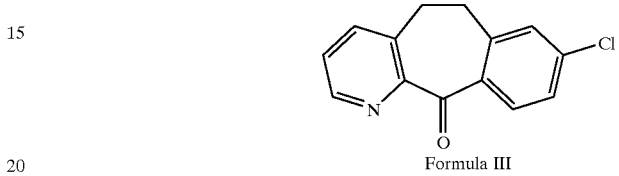

A suspension of 3-CPPA.HCl (the compound of Formula IIa) (500 g, 1.677 mol) in dichloromethane was treated at 0°–10° C. with a pre-prepared suspension of Vilsmeier's reagent (prepared by adding oxalyl chloride (10.7 g, 0.084 mol) to DMF (6.13 g, 0.084 mol) in DCM (20 mL) at 0°–10° C.). The suspension was warmed to 20°–30° C. and oxalyl chloride (158 mL, 1.81 mol) was added with the temperature being maintained in the 20°–30° C. range. The yellow suspension was stirred at 20°–30° C. and pumped into a suspension of aluminum chloride (492 g, 3.69 mol) in DCM (1.0 L) at 20°–30° C. Residual acid chloride was washed with 250 mL DCM. The dark red solution was stirred at 20°–30° C. and quenched into a pre-cooled (−10° C.) solution of water (300 mL) and 10M NaOH (250 mL), keeping the temperature below 30° C. The phases were separated and the water phase washed with DCM (250 mL). The combined DCM solution was concentrated to about 175 mL and extracted twice with 1M HCl (2.5 L each time). The combined aqueous solutions were heated to 60° C. to remove DCM. Charcoal (30 g) and celite (20 g) were added and the solution filtered, and washed through with 500 mL of 3% HCl. The filtrate was cooled to 30° C. and basified with 10M NaOH (550 mL). The product was filtered and washed with warm water and dried at 60–70° C. in vacuo to afford 386 g (94%) of 8-chloro-5,6-dihydro-11H-Benzo[5,6]cyclohepta[1,2-b]pyridin-11-one (Formula III). This material was 99% pure by HPLC assay against a standard and contained <0.5% of 10-chloro-isomer (Formula IIIa).

Example 3

By Products of Alkylation and Cyclization

By varying the arylalkyl halide in the alkylation step 1) of the present process, certain by-products can be synthesized. Illustrative by-products (compounds 6, 7, 9 and 13) are shown below.

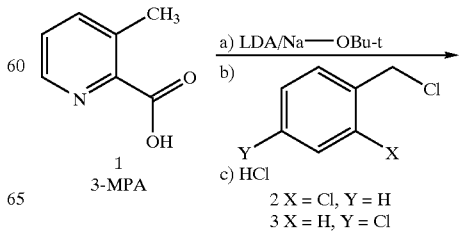

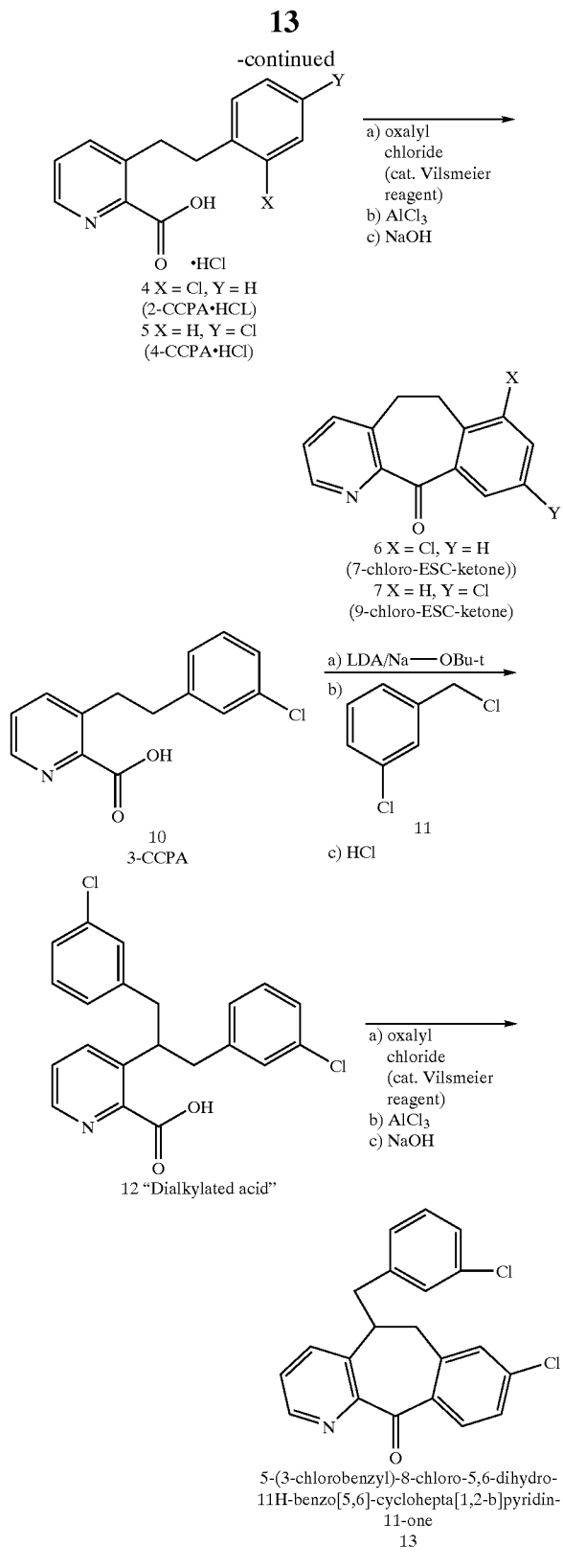

benzo[5,6]cyclohepta[1,2-b]pyridin-11-ones (7 and 9-chloro-ESC-ketones)].

3-(3-chlorophenethyl)picolinic acid (3-CPPA) itself also has been alkylated with 3-chlorobenzyl chloride under the same conditions previously outlined in the above examples, to form compound 12, which was cyclized to form compound 13.

The products derived from 3-MPA and 2 and 4-chlorobenzyl chlorides were cyclized to the respective ketones: [7 and 9-chloro-5,6-dihydro-11-H-benzo[5,6] cyclohepta[1,2-b]pyridin-11-ones (7 and 9-chloro-ESC-ketones)]. The product derived from 3-CPPA was cyclized to 5-(3-chlorobenzyl)-8-chloro-5,6-dihydro-11-H-benzo[5,6] cyclohepta[1,2-b]pyridin-11-one under the conditions outlined in the procedures above.

What is claimed is:
1. A process of making a compound of Formula III wherein X is halogen,

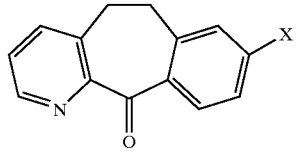

Formula III and pharmaceutically acceptable salts thereof, comprises:
a) alkylating a compound of Formula I

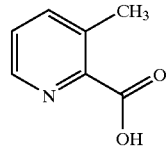

Formula I with a compound of formula Y-X, where Y is arylalkyl group, and X is a halogen, in the presence of a lithium amide and an additional base, to form an acid hydrochloride compound of Formula IIa:

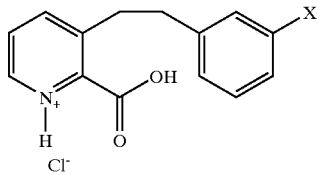

Formula IIa b) converting the acid hydrochloride of Formula IIa into an intermediate of Formula IIb:

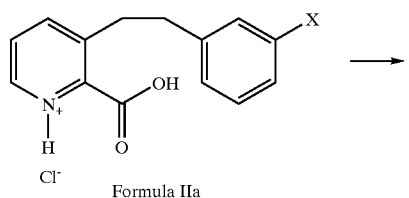

Formula IIa

-continued

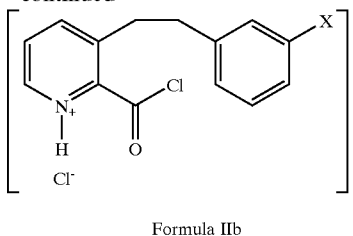

Formula IIb and c) cyclizing the compound of Formula IIb into the compound of Formula III:

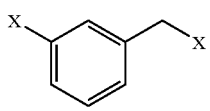

Formula IIb

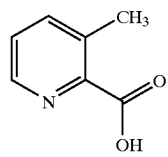

Formula III the steps b) and c) being done in one pot.

2. The process of claim 1 wherein the compound of formula Y-X is the arylalkyl halide of Formula IV:

Formula IV wherein X is a halogen.

3. The process of claim 1 wherein said step b) takes place in the presence of Vilsmeier's reagent.

4. The process of claim 1 wherein said lithium amide is a lithium dialkylated amide.

5. The process of claim 4 wherein said lithium amide is lithium diisopropylamide.

6. The process of claim 1 wherein said step a) the compound of Formula I:

Formula I is mixed with a solvent, lithium amide and an additional base of formula M—Ot—Bu, where M is sodium or potassium.

7. The process of claim 6 wherein the mole ratio of the compound of Formula I to LDA to M—Ot—Bu is 1:2:1.

8. The process of claim 7 where the solvent is triethylamine and THF.

9. The process of claim 8 wherein said step c) takes place in the presence of a solvent, oxalyl chloride, dimethylformamide and aluminum chloride.

10. The process of claim 9 wherein said solvent of step c) is dichloromethane.

11. The process of claim 10 wherein the dimethylformamide is 2 mole % with respect to the compound of Formula IIa.

12. The process of claim 1 wherein said compound of Formula III is isolated from said reaction mixture by quenching with ice and sodium hydroxide followed by concentration of the organic layer.

13. The process of claim 10 wherein said compound of Formula III is extracted as a hydrochloride salt with hydrochloric acid to form an acid extract containing said compound of Formula III.

14. The process of claim 13 wherein said acid extract is filtered with charcoal and said compound of Formula III is separated from the acid extract by adjusting pH of the acid extract to >7.

15. The process of claim 1, wherein X is chloro or bromo.

16. The process of claim 1 wherein said alkylation is carried out within a temperature range of from about −40° C. to about 30° C.

17. A process of making a compound of Formula VI:

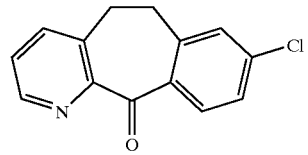

Formula VI and pharmaceutically acceptable salts thereof, comprises:

a) mixing a compound of Formula I:

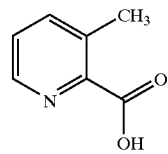

Formula I with a solvent comprising triethylamine, THF or a combination thereof, lithium amide and an additional base of formula M—Ot—Bu, where M is sodium or potassium;

b) reacting the mixture of step a) with a compound of Formula IV:

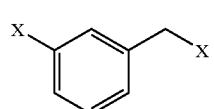

Formula IV where X is Cl; to form an acid hydrochloride compound of Formula IIa:

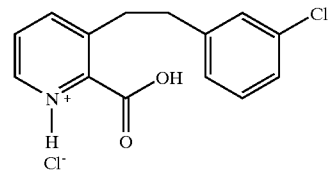

Formula IIa c) converting the acid hydrochloride of Formula IIa into an intermediate of Formula IIb in the presence of Vilsmeier's reagent;

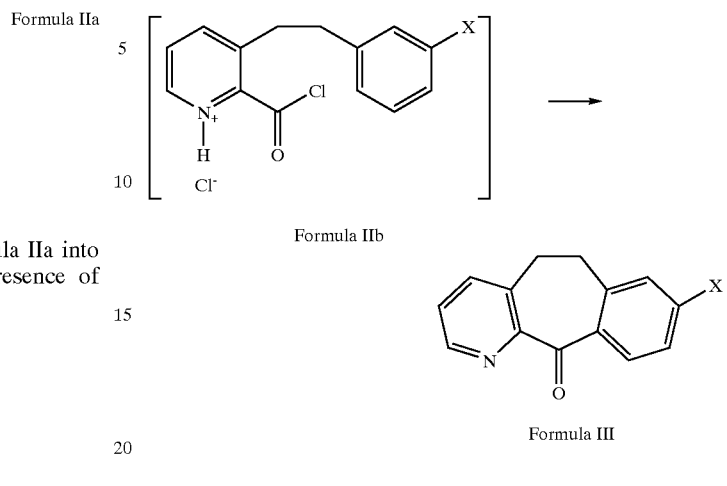

Formula IIa

Formula IIb and d) cyclizing the compound of Formula IIb into the compound of Formula III:

Formula IIb

Formula III the steps c) and d) being done in one pot.

18. The compound of Formula III prepared by the process of claim 1.

19. The compound of Formula III prepared by the process of claim 2.

20. The compound of Formula III prepared by the process of claim 17.

* * * * *